(12) United States Patent
Loyen et al.

(10) Patent No.: US 10,118,997 B2
(45) Date of Patent: *Nov. 6, 2018

(54) FINE POWDER OF POLYAMIDE FROM RENEWABLE MATERIALS AND METHOD FOR MAKING SUCH A POWDER

(71) Applicant: ARKEMA FRANCE, COLOMBES (FR)

(72) Inventors: Karine Loyen, Pont-Audemer (FR); Eric Labonne, Bernay (FR)

(73) Assignee: ARKEMA FRANCE, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/412,644

(22) Filed: Jan. 23, 2017

(65) Prior Publication Data

US 2017/0130008 A1  May 11, 2017

Related U.S. Application Data

(62) Division of application No. 12/867,394, filed as application No. PCT/FR2009/050160 on Feb. 3, 2009, now Pat. No. 9,552,614.

(60) Provisional application No. 61/042,856, filed on Apr. 7, 2008.

(30) Foreign Application Priority Data

Feb. 15, 2008 (FR) ..................... 08 50994

(51) Int. Cl.
| | |
|---|---|
| C08G 69/02 | (2006.01) |
| C08J 3/12 | (2006.01) |
| A61K 8/88 | (2006.01) |
| A61K 47/34 | (2017.01) |
| A61Q 1/12 | (2006.01) |
| C09D 5/08 | (2006.01) |
| A61K 8/02 | (2006.01) |
| C08G 69/08 | (2006.01) |
| C08G 69/26 | (2006.01) |
| A61K 8/25 | (2006.01) |
| A61Q 1/10 | (2006.01) |
| C08K 3/36 | (2006.01) |
| C09D 7/65 | (2018.01) |
| C09D 7/40 | (2018.01) |
| A61K 9/16 | (2006.01) |
| C08L 77/00 | (2006.01) |

(52) U.S. Cl.
CPC ............ *C08J 3/12* (2013.01); *A61K 8/022* (2013.01); *A61K 8/0245* (2013.01); *A61K 8/25* (2013.01); *A61K 8/88* (2013.01); *A61K 47/34* (2013.01); *A61Q 1/10* (2013.01); *A61Q 1/12* (2013.01); *C08G 69/08* (2013.01); *C08G 69/26* (2013.01); *C08K 3/36* (2013.01); *C09D 5/08* (2013.01); *C09D 7/65* (2018.01); *C09D 7/69* (2018.01); *A61K 9/1694* (2013.01); *A61K 2800/412* (2013.01); *A61K 2800/652* (2013.01); *C08J 2377/00* (2013.01); *C08J 2377/02* (2013.01); *C08L 77/00* (2013.01)

(58) Field of Classification Search
CPC ..................................................... C08G 69/04
See application file for complete search history.

(56) References Cited

U.S. PATENT DOCUMENTS

| | | | |
|---|---|---|---|
| 4,069,184 A | 1/1978 | Ferraro et al. | |
| 4,927,860 A | 5/1990 | Hilaire et al. | |
| 5,498,733 A | 3/1996 | Ayorinde | |
| 6,146,762 A | 11/2000 | D'Herbecourt et al. | |
| 9,552,614 B2 * | 1/2017 | Loyen ................ | A61K 8/0245 |
| 2006/0127424 A1 | 6/2006 | Asano et al. | |

FOREIGN PATENT DOCUMENTS

| | | |
|---|---|---|
| DE | 4421454 A1 | 12/1995 |
| JP | 5070598 A | 3/1993 |
| JP | 2002080629 A | 3/2002 |
| JP | 2004051751 A | 2/2004 |
| JP | 2008038037 A | 2/2008 |
| JP | 2008120687 A | 5/2008 |

OTHER PUBLICATIONS

English machine translation of Nakayama et al. (JP 2004-51751); generated Mar. 24, 2016.
Olivier Lecoq "Etude de la broyabilite de differents materiaux pulverulents a l'aide d'air", Memoire De These, Dec. 19, 1997, XP002497047, Universite de Technologie de Compiegne, Retrieved from the Internet.
Anonymous: "Fiche de Donnees de Securite: Rilsan Poudres Cosmetiques": Arkema, Nov. 14, 2007, pp. 1-7, XPOO2497046.

* cited by examiner

*Primary Examiner* — Michael F Pepitone
(74) *Attorney, Agent, or Firm* — Millen, White, Zelano and Branigan, P.C.

(57) ABSTRACT

The present invention relates to a powder of polyamide PA (homopolyamide or copolyamide) derived at least partially from renewable materials, in which the particles have a nonspherical shape and a volume median diameter of less than or equal to 20 μm. The present invention also relates to a process for preparing such a powder.

26 Claims, No Drawings

FINE POWDER OF POLYAMIDE FROM RENEWABLE MATERIALS AND METHOD FOR MAKING SUCH A POWDER

FIELD OF THE INVENTION

The present invention relates to fine powders, such as those using cosmetics, pharmacy or perfumery. The present invention relates more particularly to a fine powder of polyamide derived from renewable materials. The invention also relates to a process for the manufacture of such a powder derived from renewable starting materials.

In conventional cosmetics, ingredients of petroleum origin or of synthetic origin are essentially found. The processes for obtaining them are sometimes considered to be environmental pollutants.

This is because the starting materials used for the synthesis of these ingredients are obtained by steamcracking or catalytic cracking of petroleum fractions. The use of these materials contributes to increasing the greenhouse effect. Given the decrease in worldwide petroleum reserves, the source of these starting materials is gradually going to run out.

Starting materials derived from biomass are from a renewable source and have a reduced impact on the environment. They do not require all the refining steps (they are expensive in terms of energy) of petroleum products. $CO_2$ production is reduced such that they make less of a contribution to global warming.

It therefore appears to be necessary to have synthetic processes which are not dependent on starting material of fossil origin, but rather use starting materials of renewable origin.

Today, consumers are increasingly attracted by products of plant origin which have the reputation of being safer and more compatibles with the skin.

Moreover, in a market where there is as much competition as in the cosmetics market, formulators must meet the demand by consumers for cosmetics which combine effectiveness, innovative texture and sensory qualities. However, these properties depend both on the starting materials and on the processes used.

Furthermore, the emergence of cosmetic products for men, and which make it possible to meet their own expectations or requirements, also require the search for new, more suitable starting materials.

The objective of the present invention is therefore to provide a polymer powder which meets the various requirements mentioned above, both in terms of effectiveness, texture and sensory qualities and in terms of ecological and biological ethics.

PRIOR ART

By way of examples of powders commonly used in cosmetics, mentioned may be made of those of mineral origin (talc, silica, kaolin, sericite, calcium carbonate or magnesium carbonate); oxides ($TiO_2$, $ZnO$); those of plant origin (starch); those of animal origin (silk powder); and those of synthetic origin: poly(methyl methacrylate) (PMMA), polyamide 12 (PA 12).

The powders of mineral origin have sensory properties that are inferior to those of the synthetic powders. They are often rough and dry to the touch. They can dry out the skin and cause irritations.

Polyamide 12 powders, although of petroleum origin, are particularly appreciated in cosmetics for the characteristic silky and soft feel that they confer on the formulations. PA 12 is found both in make-up formulations (eye shadows, foundation, lipstick, mascara, etc.), care formulations (day creams, night cream, body milk), some product formulations, etc. In order to obtain the sensory properties required for those formulations, the powders must have an average particle size of less than 100 µm, preferably less than 50 µm, and more preferably less than 20 µm.

By way of example of PA 12 powder for cosmetic formulation, mention may be made of commercial products: Orgasol 2002 EXD NAT COS (Arkema), Nylonpoly WL 10 (Création Couleurs), Covabead N12-10 (LCW), SP500 (Toray), Ubesta (UBE), Tegolon 12-20 (Evonik).

Various manufacturing processes make it possible to produce polyamide 12 powders and each result in different powder characteristics.

Mention may be made, for example, of direct process for synthesis, which produce polyamide 12 powders by polymerization of lauryl lactam or of aminododecanoic acid. Depending on the type of process, it is possible to obtain perfectly spherical, nonporous powders or else spheroidal porous powders. In the latter case, mention may be made of the PA 12 powders sold by Arkema France under the name OROASOL Moreover, dissolution/precipitation processes exist which produce polymer powders by dissolution of a polymer in a solvent, and then reprecipitation in the form of a powder. This type of process produces spheroidal powders of varying porosity.

For example, patent application DB4421454 describes a process for synthesizing polyamide 12 powder by dissolution and precipitation, the aim of the invention in this application being to obtain a PA 12 powder of spherical shape and with a narrow particle size. The process used requires the use of a polyamide having a molecular mass and a viscosity which are sufficiently high to allow its precipitation. Thus, the powder obtained after precipitation has a diameter such that milling under severe conditions is necessary in order to obtain a fine powder of diameter less than 30 □m.

However, in all the cases mentioned above, the lauryl lactam and the aminododecanoic acid polymerized in order to obtain these PA 12 powders are derived from petrochemistry. Furthermore, in order to obtain powders with a particle size of less than 20 µm, these processes use large amounts of solvents, which are themselves derived from petrochemistry.

Unlike the polyamide 12 powders, polyamide 11 (PA 11) powders are manufactured from starting materials of plant origin.

Plant materials have the advantage that they can be cultivated in large amounts, according to demand, on the majority of the globe, and of being renewable. A renewable starting material is a natural animal or plant resource, the stock of which can be reconstituted over a short period on the human scale. In particular it is necessary for the stock to be able to renew itself as quickly as it is consumed.

PA 11 is produced by the company Arkema. An entire range of PA 11-based products exists, under the trade name RILSAN 11 or RILSANB. The base starting material for these products is castor oil, extracted from the plant of the same name (common castor), from the castor beans. Conventionally, PA 11 powders are obtained by a process of milling a prepolymer, using an impact mill. Such an impact mill comprises a rotor-stator device which performs mechanical milling. The rotor has pins or hammers, by virtue of which the product is projected against a notched arch formed by the stator. According to this current process, the product is milled by impact, collisions or attrition and the particles of powder obtained are of different shapes which are more or less angular.

However, the characteristics, in particular particle size (generally greater than 100 µm) and/or shape characteristics, of these PA 11 powders of the prior art do not make it possible to use them as cosmetic powders with sensory properties suitable for make-up and care applications (such as day creams, night creams, or sun creams). In particular, it is not possible, with the industrial process for manufacturing PA 11 used today, to obtain particles of powder with an average diameter of less than 30 µm.

Patents EP1847559 and U.S. Pat. No. 6,127,513 describe processes for obtaining polyamide powders, in particular PA 11 or 12 powders, by direct synthesis or by dissolution-precipitation, resulting in porous or nonporous, spherical powders with a particle size of less than 100 µm. However, these powders are systematically obtained in solvent, and they therefore have a not insignificant environmental impact.

The PA 11 or 12 powders of the prior art, whether they are derived from a direct synthesis process, from a dissolution-precipitation process or else derived from a process of milling a prepolymer, do not therefore make it possible to meet all the abovementioned requirements.

In addition to the PA 11 powders, all sorts of polyamide, homopolyamide or copolyamide powders, that can be obtained from renewable starting materials, exist.

Mention may, for example, be made of polyamides and copolyamides comprising the monomers 10.10 or 10.36, which can be manufactured entirely from renewable starting materials, such as plant oils and fatty acids. According to another alternative, the polyamide powders may be "mixed", i.e. based on polyamide manufactured partially from renewable starting materials. This is, for example, the case of homopolyamide 6.10 in which only the sebacic acid (C10) is of renewable origin. It is also the case of copolyamide 11/10.T, in which only the terephthalic acid (T) is not of renewable origin.

These copolyamide powders are produced by the company Arkema according to a cryogenic milling process. The manufacturing process used today does not make it possible to obtain particles with an average size of less than 30 pun.

The objective of the present invention is therefore to design a new polyamide powder or copolyamide powder which is both of renewable origin and high performance, and for which the production process does not require the involvement of chemical or technological manipulations which are laborious, energy-expensive or polluting.

The objective of the present invention is also to provide a process for the manufacture of ultrafine PA powder which is simple, rapid (comprising as few steps as possible) and easy to implement.

The objective of the present invention is also to provide a process which is modulatable and flexible, i.e. which can be readily and rapidly adjusted according to the desired powder particle size, and which adapts readily to the existing manufacturing devices in the powder industry.

Armed with its expertise in the manufacture of high-performance bioresourced polyamide, the applicant company has now found a new ultrafine polyamide powder derived from renewable starting materials, and of which the preferred, but not exclusive, fields of use are cosmetics, pharmacy and perfumery. The applicant has also found a process for the manufacture of such particles of PA powder having an average diameter of less than 30 µm.

SUMMARY OF THE INVENTION

More specifically, a subject of the present invention is a powder of polyamide PA (homopolyamide or copolyamide) derived at least partially from renewable materials, in which the particles are nonspherical in shape and have an average diameter (volume median diameter) of less than 30 µm.

Advantageously, said polyamide powder comprises at least one of the following molecules: 11-aminoundecanoic acid, n-heptyl-1-amino undecanoic acid, sebacic acid, decanediamine, a difatty acid, a dimer of a fatty acid, and mixtures thereof.

Advantageously, said polyamide PA of the powder according to the invention is chosen from PA 11, PA 10.10, and copolyamides comprising at least one of the following monomers: 11, 10.10, 10.36, 6.10, 10.T, and mixtures thereof.

Advantageously, said polyamide (homopolyamide or copolyamide) is derived entirely from renewable materials.

Advantageously, the polyamide powder of the invention is PA 11.

Advantageously, the particles of polyamide PA powder of the invention have a specific surface area within the range of from 1 to 20 $m^2/g$, preferably from 2 to 10 $m^2/g$, preferably from 3 to 6 $m^2/g$.

Advantageously, said particles have a volume median diameter of less than 20 µm, preferably within the range of from 5 to 15 µm.

Advantageously, the absorption capacity of the powder of the invention, measured according to standard DIN ISO 787N, is within the range of from 50 to 180 g of oil/100 g of polyamide powder, preferably from 55 to 110 g of oil/100 g of powder, preferably from 60 to 90 g of oil/100 g of powder.

Advantageously, the breaking strength of said powder, when it is compacted only by compression under one tonne, is within the range of from 100 to 600 Newtons, preferably from 150 to 500 Newtons. Advantageously, the powder according to the invention comprises $^{14}C$. Advantageously, said powder comprises at least 20% by mass of carbon of renewable origin, preferably 50% by mass of carbon of renewable origin.

Advantageously, said powder comprises at least $0.2\times10^{-10}$% by mass of $^{14}C$, preferably $0.6\times10^{-10}$% by mass of $^{14}C$.

A subject of the present invention is also the use of powder as defined above in cosmetic, pharmaceutical or perfumery products. Said powder may advantageously be used as a compacting agent in compact cosmetic formulations or else as a matifying agent.

A subject of the present invention is also a process for the preparation of natural polyamide powder as defined above, comprising milling a powder of prepolymer having an inherent viscosity of less than 0.5 (according to the Arkema method: 0.5 g/dl in metacresol at 25° C.), preferably within the range of from 0.25 to 0.5 (according to Arkema method: 0.5 g/dl in metacresol at 25° C.). Advantageously, silica, preferably fumed silica, may be added to the prepolymer powder before it is milled in the process of the invention.

Advantageously, the milling according to the process of the invention is atmospheric milling, i.e. carried out at ambient temperature. Advantageously, said milling is carried out by means of an opposed air jet mill.

Advantageously, said process comprises, before the milling step, a step of manufacture of a prepolymer of PA having a number-average molecular mass of less than 5000 g/mol, preferably within the range of from 500 to 3000 g/mol (number-average molecular mass determined by size exclusion chromatography, using HFIP as solvent, and refractometric detection), and having a viscosity of less than 0.5 (according to Arkema method: 0.5 g/dl in metacresol at 25° C.).

Advantageously, said process comprises, after the milling step, a step of rise in viscosity of the milled prepolymer particles, to the final viscosity desired for the powder.

Advantageously, the viscosity rise is performed by solid-phase polycondensation in a dryer. Advantageously, the various steps of the process of the invention do not involve a solvent.

Advantageously, the final particle size of the PA powder is directly adjusted by adjusting the milling speed. Advantageously, the milling speed is adjusted by means of a selector integrated into the mill.

A subject of the present invention is also a cosmetic powder as defined above, containing an additive chosen from pigments, fillers, antioxidants and powder binders. Advantageously, said cosmetic powder contains silica powder. Advantageously, said cosmetic powder constitutes a face powder or an eye shadow.

The powder according to the invention may advantageously be used in coatings, paints, anticorrosive compositions, additives for paper, powder agglomeration technologies by melt agglomeration or radiation sintering for manufacturing objects, electrophoresis gels, multilayer composite materials, the packing industry, the toy industry, the textile industry, the automobile industry and/or electronics industry.

DETAILED DESCRIPTION

The particles of polyamide (homopolyamide or copolyamide) powder of the invention are derived (entirely or only partly) from renewable starting materials of plant origin, this being characterized in that said particles comprise carbon of renewable origin.

For the purposes of the invention, the term "polyamide" is intended to mean the products of condensation of lactams, of amino acids or of diacids with diamines and, as a general rule, any polymer formed from units connected to one another by amide groups.

The expression "polyamide of entirely renewable origin which is part of the composition of powder according to the invention" is intended to mean:

aliphatic polyamides obtained from lactams or amino acids (such as, for example, PA 11 obtained by polycondensation of 11-aminoundecanoic acid);

the products of condensation of a dicarboxylic acid with a diamine (such as, for example, PA 10.10, which is a product of the condensation of decanediamine with sebacic acid, of as PA 10.36, which is a product of the condensation of decanediamine with a fatty acid dimer);

copolyamides resulting from the polymerization of various monomers, such as those mentioned above, for instance the following copolyamides: PA 11/10.10, PA 11/10.36, PA 10.10/10.36, the 11-aminoundecanoic/n-heptyl-11-aminoundecanoic copolyamide, etc. The copolyamides of renewable origin, which comprise at least two monomers, are more particularly described in French Patent Application No.: 07.53319.

The term "monomer" in the present description of the copolyamides should be taken to mean "repeating unit". In fact, the case where a repeating unit of the PA consists of the association of a diacid with a diamine is specific. It is considered that it is the association of a diamine and of a diacid, i.e. the diamine.diacid pair (in equimolar amount), which corresponds to the monomer. This is explained by the fact that, individually, the diacid or the diamine is just a structural unit, which is not sufficient by itself to polymerize.

By way of examples of amino acids of renewable origin, mention may be made of 11-aminoundecanoic acid produced from castor oil for example, 12-aminododecanoic acid produced from castor oil for example, 10-aminodecanoic acid produced from decylenic acid obtained by metathesis of oleic acid for example, 9-aminononanoic acid produced from oleic acid for example.

By way of examples of diacids of renewable origin, mention may be made of, according to the number x of carbons of the molecule (Cx):

C4: succinic acid from glucose for example;
 C6: adipic acid from glucose for example;
 C7: heptanedioic acid from castor oil;
 C9: azelaic acid from oleic acid (ozonolysis) for example;
 C10: sebacic acid from castor oil for example;
 C11: undecanedioic acid from castor oil;
 C12: dodecanedioic acid from biofermentation of dodecanoic acid=lauric acid (castor oil: coconut and cabbage palm oil) for example;
 C13: brassylic acid from rucic acid (ozonolysis) which is found in rapeseed for example;
 C14: tetradecanedioic acid by biofermentation of myristic acid (castor oil: coconut and cabbage palm oil) for example;
 C16: hexadecanedioic acid by biofermentation of palmitic acid (mainly palm oil) for example;
 C18: octadecanedioic acid obtained by biofermentation of stearic acid (a little in all plant oils, but predominant in animal fats) for example;
 C20: eicosanedioic acid obtained by biofermentation of arachidic acid (predominant in rapeseed oil) for example;
 C22: docosanedioic acid obtained by metathesis of undecylenic acid (castor oil) for example
 C36: fatty acid dimer derived from the by-products of resins converted by the Kraft process.

By way of examples of diamines of renewable origin, mention may be made of, according to the number x of carbons of the molecule (Cx):

C4: butanediamine obtained by amination of succinic acid;
 C5: pentamethylenediamino (from lysine);
 and so on for the diamines obtained by amination of the diaoids of renewable origin seen above.

The term "polyamide of partially renewable origin", i.e. derived only in part from renewable materials (referred to in the text as "mixed" polyamide), is intended to mean:

the products of condensation of a dicarboxylic acid with a diamine, and in which only one of the two (the diacid or the diamine) is of renewable origin. This is the case of PA 6.10 for example, since, in the 6.10 monomer, only the sebacic acid is of renewable origin, whereas the hexamethylenediamine is derived from petrochemistry;

the copolyamides resulting from the polymerization of various monomers (renewable, non-renewable or mixed) such as those mentioned above. This is the case, for example, of CoPA 6.6/10.10 in which the "6.6" monomer is of non-renewable origin, whereas the "10.10" monomer is of renewable origin. This is also the case of PA 11/10.T for example, which comprises a monomer of renewable origin ("11") and a mixed monomer of partially renewable origin ("10.T") since only the decanediamine is of renewable origin, whereas the terephthalic acid (T) is not.

Although, in accordance with a preferred embodiment of the invention, the present invention is generally described in the rest of the text with reference to a PA 11 powder, which has the advantage of being entirely of renewable origin, the present invention is obviously not limited to PA 11 powders. The present invention includes any PA (homopolyamide or copolyamide) powder derived entirely or partially (in the case of mixed polyamides) from renewable starting materials, and in which the particles are nonspherical in shape and have a volume median diameter of less than 30 μm.

The expression "polyamide (homopolyamide or copolyamide) powder of renewable origin" is intended to mean polyamide powders which comprise carbon of renewable origin.

In fact, unlike materials derived from fossil materials, materials composed of renewable starting materials contain $^{14}C$. All carbon samples taken from living organisms (animals or plants) are in fact a mixture of 3 isotopes: $^{12}C$ (representing ~98.892%), $^{13}C$ (~1.108%) and $^{14}C$ (traces: $1.2 \times 10^{-12}$%). The $^{14}C/^{12}C$ ratio of living tissues is identical to that of the atmosphere. In the environment, $^{14}C$ exists in two predominant forms: in inorganic form, i.e. in the form of carbon dioxide ($CO_2$), and in organic form, i.e. in the form of carbon integrated into organic molecules.

In a living organism, the $^{14}C/^{12}C$ ratio is kept constant by the metabolism since carbon is continually exchanged with the environment since the proportion of $^{14}C$ is constant in the atmosphere, the same is true in the organism, while it is alive, since it absorbs this $^{14}C$ like it absorbs the $^{12}C$. The average $^{14}C/^{12}C$ ratio is equal to $1.2 \times 10^{-12}$.

$^{12}C$ is stable, i.e. the number of $^{12}C$ atoms in a given sample is constant over time. $^{14}C$ is itself radioactive (each gram of carbon of a living being contains sufficient $^{14}C$ isotope to give 13.6 disintegrations per minute) and the number of such atoms in a sample decreases over time (t) according to the law:

$$n = no \exp(-at)$$

in which:
no is the number of $^{14}C$ at the origin (at the death of the creature, animal or plant),
n is the number of $^{14}C$ atoms remaining after time t,
a is the disintegration constant (or radioactive constant); it is linked to the half-life.

The half-life (or half-period) is the period of time after which any number of radioactive nuclei or of unstable particles of the given species is reduced by half by disintegration; the half-life $T_1 a$ is linked to the disintegration constant a by the formula $aT_{1/2} = \ln 2$. The half-life of $^{14}C$ is 5730 years.

Given the half-life ($T_{1/2}$) of $^{14}C$, it is considered that the $^{14}C$ content is constant from the extraction of the plant starting materials to the manufacture of the polymer, and even to the end of its use.

The applicant considers that a polymer (in this case polyamide) is derived from renewable starting materials if it contains at least 20% by mass of C of renewable origin out of the total mass of carbon, preferably at least 50% by mass of C of renewable origin out of the total mass of carbon.

In other words, a polymer (polyamide in the case of the invention) is derived from renewable starting materials if it contains at least $0.2 \times 10^{-10}$% by mass of $^{14}C$, preferably $0.6 \times 10^{-10}$% by mass of $^{14}C$.

At the current time, at least two different techniques exist for measuring the $^{14}C$ content of a sample:

By liquid scintillation spectrometry: this method consists in counting "beta" particles derived from the disintegration of $^{14}C$: the beta-radiation derived from a sample of known mass (known number of $^{12}C$ atoms) is measured for a certain period of time. This "radioactivity" is proportional to the number of $^{14}C$ atoms, which can thus be determined. The $^{14}C$ present in the sample emits ß-radiation, which, in contact with the liquid scintillant (scintillator), produces photons. These photons have different energies (between 0 and 156 Key) and form what is called a $^{14}C$ spectrum. According to two variants of this method, the analysis relates either to the $CO_2$ produced beforehand by the carbon-based sample in an appropriate absorbent solution, or to the benzene after prior conversion of the carbon-based sample to benzene.

By mass spectrometry: the sample is reduced to graphite or to $CO_2$ gas, and analysed in a mass spectrometer. This technique uses an accelerator and a mass spectrometer to separate the $^{14}C$ ions from the $^{12}C$ ions and therefore to determine the ratio of the two isotopes.

All these methods for measuring the $^{14}C$ content of materials are described precisely in the ASTM D 6866 standards (notably D6866-06) and in the ASTM D 7026 standards (notably 7026-04). These methods measure the $^{14}C/^{12}C$ ratio of a sample and compare it with the $^{14}C/^{12}C$ ratio of a reference sample of 100% renewable origin, so as to give a relative percentage of C of renewable origin in the sample.

The method of measurement preferably used in the case of the polyamides of the invention is the mass spectrometry described in the ASTM D6866-06 standard ("accelerator mass spectroscopy").

The particles of polyamide powder according to the invention, such as PA 11, have an irregular nonspherical shape. Said particles do not have any sharp edges, which gives them a sliding rolling effect to the touch.

The average diameter (volume median diameter) of the particles of polyamide of the invention is less than 30 μm, preferably less than or equal to 20 μm, and more preferably within the range of from 5 to 15 μm, or better still substantially equal to 10 μm.

Advantageously, the specific surface area of the particles of powder according to the invention is within the range of from 1 to 20 m²/g, preferably from 2 to 10 m²/g, preferably from 3 to 6 m²/g. Advantageously, the absorption capacity of said particles, measured according to the DIN ISO 787N standard, is within the range of from 55 to 110 g of oil/100 g of powder, preferably from 60 to 90 g of oil/100 g of PA powder.

The powder of the invention has sebum-controlling properties, and also a matifying effect. It is therefore entirely suitable for cosmetic products for use in making up and/or caring for human skin, in particular of the face, the neck and the body, and also for pharmaceutical products or perfumery products (fragrancing powder for the body or the feet, for example).

Advantageously, the powders of the invention, by virtue of their shape, their particle size and their specific surface area, of improved sensory properties and also improved compacting properties and oil absorption properties, compared with the polyamide powders of the prior art.

Powders, having a diameter substantially equal to 10 μm, of PA 12 (of non-renewable origin) and of PA 11 (renewable origin) were assessed in free form by a trained sensory panel made up of 10 individuals. The descriptors used as listed hereinafter. They are assessed on a scale ranging from 1 to 10. On this scale, "1" represents inferior spreading, covering capacity and velvet-softness properties, whereas "10" represents superior spreading, covering capacity or velvet-softness properties.

Ease of Spreading:

Definition: Characterizes the ease with which the powder is spread.

Protocol: Take a spatula-tip of powder, place it on the snuffbox and spread it out into a thin layer.

Evaluation: Note how easy it is to spread the powder (sliding sensation).

Covering Capacity:

Definition: Characterizes the property of the powder with respect to covering the skin uniformly, whitening.

Protocol: Take a spatula-tip of powder, place it on the snuffbox and perform a sweeping motion with the hand (spread the powder out with the hand in a forwards and backwards movement).

Evaluation: Note the homogeneity of the spreading and the uniformity of the layer, visually.

Velvet-Softness

Definition: Characterizes a first sliding sensation (velvet-softness, creamy) which remains unchanged throughout the period.

Protocol: Take a pinch between the fingers and perform small circular movements without pressure.

Evaluation: Note the feeling of softness over the period.

TABLE 1

Results (mean of marks) of the sensory tests carried out on milled PA 11 and milled PA 12

|  | Spreading | Coverage | Velvet-softness |
|---|---|---|---|
| Milled polyamide 11 | 8 | 4.3 | 3 |
| Milled polyamide 12 | 4.5 | 6 | 3.2 |

The results of the sensory analysis show that the polyamide 11 powder obtained according to the process of the invention exhibits the same level of velvet-softness as the polyamide 12 powder obtained by milling according to the process described in Patent Application DE 4421454. Polyamide 11 and polyamide 12 exhibit similar sensor properties.

Furthermore, the milled polyamide 11 powder exhibits a spreading capacity that is superior to that of the polyamide 12 powder, correlated with an inferior covering capacity which provides a natural finish. This characteristic is linked to the particle size distribution, and can be easily adjusted according to the milling conditions, by virtue of the process of the invention.

Furthermore, the PA powder of the invention, in particular by virtue of the nonspherical shape of its particles, exhibits improved compacting properties, compared with the other polyamide powders obtained according to the processes of the prior art (which are spherical in shape), which makes it possible to use it advantageously as a compacted make-up powder, in particular as a face powder or an eye shadow.

Thus, the breaking strength of said powder, when it is compacted only by compression under one tonne, is within the range of from 100 to 600 Newtons, preferably from 150 to 500 Newtons.

The compaction capacity is evaluated in the following way:

1—Preparation of the Compact

Each compact is prepared with 0.5-0.002 g of powder so as to produce a disc 13 mm in diameter. The compression is carried out in three phases:

1st compression at 1 tonne: during this first phase, the pressure on the compact falls very quickly (reduction of the air and optimal stacking of the powder). After 5 seconds, the pressure is released.

2nd compression at 1 tonne: the powder compacts and the pressure falls very little. After 5 seconds, the pressure is released.

3rd compression at 1 tonne of the powder for 5 seconds.

After these 3 series of compression, the powder is compacted in the form of a tablet 13 mm in diameter and 4.5 mm thick.

2—Measurement of Compact Cohesion

The mechanical trial for testing these compacts is very commonly used in pharmacy for characterizing tablets (diametral breaking test or "Brazilian" test). This test consists in applying a force perpendicular to the direction of compression (i.e. to the edge of the compact) until the tablet breaks.

Table 2 below gives the results of breaking strength for various types of polyamide powder.

TABLE 2

Results of the breaking tests for various types of PA powder

|  | Breaking strength (Newtons) | Remark |
|---|---|---|
| Milled PA 11 powder (10 μm) | 160 |  |
| Milled PA 11 powder (100 μm) | 5 |  |
| Spherical PA 12 powder (10 μm) | 0 | No compaction |
| Porous spheroidal PA 12 powder (10 μm) | 240 |  |

Table 2 shows that a spherical PA 12 powder cannot be compacted. The same would be true of a spherical PA 11 powder. On the other hand, the PA 11 powder obtained by the novel milling process compacts very well, since a tablet is obtained which holds mechanically only by compression, without the addition of a fatty compound. The mechanical strength of the tablet obtained is slightly less than that obtained with the porous spheroidal polyamide 12 powder developed specifically for this compaction property. The PA 11 powder according to the invention can therefore be advantageously used as a compacting agent, particularly suitable for cosmetic formulations of pressed powders.

Moreover, the PA 11 powder of the invention has advantageous properties in emulsion: it reduces the tacky and greasy aspect of emulsions comprising a continuous fatty phase. It leaves a mat and powdered finish on the skin which completely changes the comfort of using formulations including the powder of the invention.

In fact, cosmetic compositions comprising a continuous fatty phase very often cause inconveniences when applied, which sometimes limit their use by consumers. The continuous greasy film at the surface of the skin causes a tacky, oily and sticky sensation, which is no longer accepted by consumers today. Moreover, the shiny and oily aspect is detrimental to the cosmetic and aesthetic properties of these creams. The application of a make-up after the application of day cream or sun cream is made difficult because of this tacky effect which interferes with the spreading of the make-up on the skin. The application of make-up is therefore disrupted leading to a non-uniform appearance. Over time, poor fastness of the make-up and also transfer and loss of the colours of the make-up are also witnessed.

In order to reduce the oily, tacky and sticky aspect of these compositions comprising a continuous fatty phase, it is known practice to add volatile oils such as silicone oils, but they do not play the protective role associated with a continuous fatty phase and do not have humectant properties on the skin. Moreover, the polyols generally added to the formulations for their humectant and moisturizing properties on the skin introduce a persistent sticky effect, which is undesirable on the skin, and which adds to that of the cosmetic oils of the composition.

It is therefore important to manufacture a cosmetic composition which answers both the sensory and aesthetic problem while at the same time fulfilling its protective role with respect to the skin, as mentioned above. A water/oil emulsion comprising a fine powder according to the invention makes it possible to solve this technical problem. In particular, it significantly reduces the greasy and sticky effect introduced by the oils and/or the polyols of cosmetic compositions. This effect is observed irrespective of the type of oil, whether or not it is volatile, whether it is or mineral, animal, plant or synthetic origin, and whether it is a hydrocarbon-based, silicone or fluoro oil.

By way of example, mention may be made of the following formulation (hereinafter referred to as "composition I") of a water/silicone emulsion and containing glycerol:

| Phase | Ingredients (INCI names) | % weight |
|---|---|---|
| A | Water | QS 100 |
|   | Magnesium sulphate | 0.70 |
|   | Disodium EDTA | 0.10 |
|   | Glycerol | 3.00 |
|   | Chlorophenesin | 0.25 |
|   | Phenoxyethanol, methylparaben, ethylparaben, butylparaben, propylparaben, isobutylparaben | 0.60 |
|   | Xanthan gum | 0.10 |
| B | Cyclopentasiloxane, PEG-10 dimethicone, Disteardimonium Hectorite | 8.00 |
|   | Cyclomethicone | 20.00 |
|   | Disteardimonium Hectorite | 1.00 |
| C | Polyamide 11 powder | 3.5 |

Manufacturing process:
The ingredients of phase A are mixed.
The ingredients of phase B are mixed.
A is added to B slowly with high-speed stirring so as to produce the emulsion.
The polyamide 11 powder is added to the emulsion with gentle stirring.

The effect of the addition of PA powders according to the invention to emulsions comprising a continuous fatty phase was measured by sensory analysis in various types of compositions. Each composition was the subject of a sensory profile study conducted by a panel of five experts, according to the following descriptors:
during the product application phase (grease, rapidity of penetration); and
immediately after application (brightness of the skin, softness of the skin, tacky skin effect).

Each composition is analysed blind by comparison of all the trials forming a series. The various criteria were evaluated on a scale ranging from 0 to 8, the value 0 indicating the absence of the designated criterion (for example, a feeling of no greasiness), the value 8 indicating a very marked tendency of the selected criterion (for example, a very substantial feeling of greasiness).

The results are given in Table 3, showing the behaviour during application of an emulsion comprising a continuous fatty phase including the powder of the invention (composition I) in comparison with the same emulsion not containing the powder of the invention (control).

Composition I comprises 3.5% of polyamide 11 powder (corresponding to Example 7 described in the subsequent text), the milling having been followed by an increase in viscosity so as to obtain a viscosity in solution of 0.8 (according to Arkema method: 0.5 g/dl in metacresol at 25° C.).

TABLE 3

|  |  | Control 0% of PA 11 | Composition I 3.5% of PA 11 |
|---|---|---|---|
| Behaviour during application | Grease | 6 | 2 |
|  | Rapidity of penetration | 1 | 5 |
| Behaviour after application | Brightness | 8 | 4 |
|  | Softness | 2 | 4 |
|  | Sticky skin | 6 | 2 |

The intrinsic characteristics of the PA 11 powder according to the invention confer on the formulations which contain it in an effective amount, a soft feel when taken up, very rapid absorption during application on the skin (for example in only 2 or 3 actions) and a mat finish on the skin. Compared with the other matifying powders of the prior art, the PA 11 powders provide a lighter velvet effect or "velvet-softness" and a natural and imperceptible finish. Natural make-up is increasingly sought by consumers.

The nonspherical powder of the present invention is therefore particularly suitable for cosmetic products, for men in particular. Said powder makes it possible to create formulations for which both the act of application and the finish on the skin are specifically masculine.

Although they are intended for the cosmetics field (for women and/or for men) in the embodiments described, the powders of the invention may be used in any of the other fields where their properties, in particular particle size and compaction properties, and their renewable origin are desired.

By way of example, the powders of the invention are particularly suitable for coatings (anticorrosive coatings, paints, etc). The powders of the invention may also be used as additives for paper or else in electrophoresis or in powder agglomeration technologies by melt agglomeration or radiation sintering, such as, for example, caused by a laser beam (laser sintering), for manufacturing objects. Said powders may also be used as spacers in composite materials, in particular between the layers of multilayer materials. Their uses in the packaging industry, the toy industry, the textile industry, the automobile industry and the electronics industry can also be envisioned.

A subject of the present invention is also a process for preparing a polyamide powder as defined above. The process is characterized in that it comprises milling a powder of prepolymer having a low inherent viscosity.

While the process of the invention is, in the present description, in accordance with a preferred (but nonlimiting) embodiment of the invention, applied to the manufacture of a powder of polyamide 11, it goes without saying that the same steps of this process are transposable in the case of the manufacture of other types of homopolyamides or copolyamides.

In a known manner, the polyamide 11 is obtained by polycondensation of 11-aminoundecanoic acid or lactam 11.

According to one embodiment of the process of the invention, the prepolymer used is a polyamide 11 having a low number-average molecular mass and a low viscosity.

In the same manner, in the case of the manufacture of another copolyamide powder, the process of the invention uses a prepolymer of CoPA having a low number-average molecular mass and a low viscosity. Advantageously, such a CoPA prepolymer comprises at least two monomers, one of which is predominant (i.e. the percentage by weight of which relative to the total weight of CoPA is greater than 50%). The predominantly monomer is advantageously chosen such that the melting point of the CoPA is not too low, but rather of the order of 170° C. for example, such that it is not necessary to carry out the milling of the invention under cryogenic conditions. Preferably, the predominant monomer of such a CoPA is 11-aminoundecanoic acid.

This low-viscosity prepolymer has the advantage that it can be very easily milled, and can therefore be milled under less strict conditions than in conventional polyamide milling processes.

The prepolymer (PA 11 or the like) of the invention has a number-average molecular mass (Mn), measured by GC, of less than 5000 g/mol, preferably within the range of from 500 to 3000 g/mol.

The term "low viscosity" is intended to mean an inherent viscosity of the prepolymer of less than 0.5 (measurement for 0.5 g/dl in metacresol at 25° C.).

The inherent viscosity of the prepolymer is advantageously within the range of from 0.25 to 0.50, preferably within the range of from 0.30 to 0.45. Of course, the inherent viscosity of the polyamide may be even lower if necessary, depending on the intended application. In fact, according to the process of the invention, the lower the viscosity of the starting prepolymer, the easier it is to mill and the smaller the average diameter of the PA powder obtained will be. By virtue of the flexibility or modularity of the process of the invention, it is therefore sufficient to adjust the viscosity of the prepolymer at the start, according to the particle size intended for the powder.

In order to obtain a low-viscosity prepolymer, 11-amino is, for example, loaded into an autoclave with 30 to 50% of water, with the optional addition of a catalyst such as phosphoric acid. The addition of a catalyst in the process of the invention is not generally necessary, and it is possible to start from a system without phosphorus-containing additive. The mixture is heated to a temperature of approximately 190° C. under a pressure of 10 bar. The water is distilled and the reactor is degassed. The vapour removed is recondensed and weighed. The amount of vapour removed is monitored until a certain amount of removed vapour is reached, which corresponds to the desired viscosity for the prepolymer. The prepolymer having an appropriate viscosity is then drained. At the emptying valve, the prepolymer is still molten, it is then cooled under the effect of the departure of the vapour from the water and is again solidified. The solidified prepolymer is then passed into a granulator or a mill, which reduces it to coarse powder having an average diameter of less than 3 mm.

At this stage, the prepolymer obtained may advantageously be subjected to compounding so as to add all sorts of additives to it, such as pigments, antioxidants, powder binders, etc. Powders of all colours can thus be manufactured. The compounding consists in mixing the PA with additives in the molten phase (for example by means of two screws in the heated sleeve). The mixture is then cooled by means of two steel rollers with circulation of cold water or else by means of a calendaring machine. The prepolymer is then reduced to granules and may be subjected to coarse milling, before feeding the mill. The mill is fed with PA continuously by means of a dual-valve chamber system.

The milling according to the invention is atmospheric milling, i.e. carried out at ambient temperature (approximately 25° C.). Such milling makes it possible to prevent the formation of sharp edges at the surface of the particles of powder, which has a considerable influence on the sensory properties, in particular the feel of the powder obtained.

Furthermore, the environmental impact of the process of the invention is much lower than that of a process of dissolution/precipitation in a solvent medium, which requires the heating and then cooling of large amounts of solvents generally derived from petrochemistry. These solvents will ultimately have to be eliminated, even if a recycling circuit makes it possible to reuse them several times.

The milling device used in the process of the invention may be of any type suitable for the manufacture of powders.

According to a preferred embodiment of the invention, the milling is carried out by means of an opposed air jet mill, by virtue of two opposed nozzles fed with compressed air, generally at 8.5 bar ($8.5 \times 10^5$ Pa). The air preferably used is filtered and dried, and it does not therefore introduce any contaminant. Of course, any other suitable gas could replace the air feeding the nozzles. The prepolymer is transported and carried along directly by the air which exits the nozzles. Under the effect of the opposed air jets, the particles of prepolymer collide with one another, thereby reducing their particle size and resulting in their characteristic final irregular shape without sharp edges.

The dimensions of the milling system and the gas inlet flow rates used are adjusted so as to obtain good fluidization and the desired particle size. By way of example, the power consumed for the milling is approximately 1 to 2 kW·h/kg of powder.

This type of mill is commonly used and very widespread in the polymer industry. The opposed air jet mill is particularly suitable for the manufacture of very fine powders having narrow particle size distribution curves. This is because, compared with the relative speed of mechanical mills (impact mills: up to 140 m/s, counter-rotating mills: up to 250 m/s), the opposed air jet mills used in the process of the invention allow much higher relative milling speeds, greater than 400 m/s.

Advantageously, the opposed air jet mill comprises an integrated classifier or selector, capable of directly adjusting the milling speed so as to obtain the desired particle size, unlike other systems which generally require providing for the addition of an ancillary adjusting device in series. The selector returns the particles having a diameter that does not comply, to the milling chamber feed system, whereas the particles having a particle size that complies with the adjustment setting are collected in an air filter. The powder can be collected directly at the bottom of this filter, in a bag for example. The adjustments to be made according to the process of the invention are the milling speed for obtaining the desired particle size, and the feed flow rate so as to maintain a constant certain amount of product in the milling chamber. The milling speed can be adjusted directly at the selector and the transitions for changing the particle size of the powder during the process of the invention are extremely rapid. The use of such an opposed air jet mill improves the productivity of the process of the invention.

The following examples illustrate a preferred embodiment of the invention, without however limiting it. The mill used in these examples is an opposed air jet mill (2 nozzles). It is a large mill with an air flow rate substantially equal to 1250 m³/h (model: MultiNO 6240, manufacturer: Schüttgutveredelung NOLL GmbH).

Example 1

Manufacture of a powder having a D50=8 µm, the D50 corresponding to the volume-average size, i.e. the value of the particle size which divides the population of particles examined exactly into two.

The adjustment setting for the speed of the selector in order to obtain a D50 of 8 µm is determined by those skilled in the art in barely a few minutes. 4 bags of 15 kg of powder (i.e. 60 kg in total) are produced with a flow rate of 60 kg/h (therefore a consumed energy of 2 kW·h/cg of powder). The selector speed is 1900 rpm. The D50 is very stable during the production:

bag No. 1: D50=8.06 µm
bag No. 2: D50=8.07 pun
bag No. 3: D50=8.11 µm
bag No. 4: D50=8.10 µm Example 2

Manufacture of a powder having a D50=12 µm:
Flow rate of 150 kg/h with selector speed of 1150 rpm 4 bags of 15 kg are manufactured, i.e. 60 kg.

Example 3

Manufacture of a powder having a D50=10 µm:
Flow rate of 100 kg/h with a selector speed of 1450 rpm. D50 values also stable:

bag No. 1: D50=10.33 µm
bag No. 2: D50=10.15 µm
bag No. 3: D50=10.08 µm
bag No. 4: D50=10.33 µm
etc.

Moreover, since the air jet mill does not comprise any milling members, this facilitates its cleaning and maintenance, and it does not show any problems of wear or of risk of contamination of the powder that can be encountered with the members of conventional milling. The air jet mill also makes it possible to avoid the risk of pollution of the powder with metal particles, compared with mills which use moving metal parts. The purity and the natural and renewable quality of the polyamide powders according to the invention are therefore preserved by virtue of this embodiment of the process of the invention.

Of course, the milling device used by the invention is not limited to this embodiment, and any other appropriate device, such as a ball mill, a bead mill, a roller mill, etc, could also be used, provided that it makes it possible to obtain a powder in accordance with that defined by the present invention.

The milling device of the process of the invention makes it possible to obtain particles of powder having an average diameter of less than 30 µm, and preferably less than 20 □m. The average diameter may advantageously be less than 5 □m by virtue of the process of the invention. The average diameter of the particles of powder obtained by the process of the invention is chosen according to the intended application. For example, for cosmetics, the average diameter of the particles of powder is advantageously within the range of from 5 to 15 µm, and it is preferably substantially equal to 10 µm.

According to one embodiment of the process of the invention, and in order to further improve the "processability" on ultrafine grains, 1% by mass of silica, preferably fumed silica, relative to the total weight (PA-silica) can be added to the prepolymer powder, prior to it being milled. Mention may, for example, be made of the products sold under the name Aerosil (such as Aerosil R972) by the company Degussa Evonik, and also the products sold under the name Cab-O-Sil by the company Cabot.

According to a preferred embodiment of the invention, the powder obtained after milling is subjected to solid-phase polycondensation in a dryer. This step, also called "drying", serves to perform a rise in viscosity of the milled prepolymer particles. During this viscosity rise step, the powder is, for example, heated (to a temperature of approximately 150° C.) under vacuum under a pressure of approximately 20 mbar absolute (i.e. 2×10³ Pa) in a rotary dryer for a varying period of time, depending on the desired final viscosity of the powder. Other suitable techniques for viscosity rise may, of course, be used in the method of the invention, such as heating with nitrogen sweeping, rotary double-cone drying or else agitated double-cone drying, etc.

According to a preferred embodiment of the invention, screening is also carried out in order to remove the agglomerates or other large particles which may have been created during the drying.

The PA (homopolyamide or copolyamide) powder obtained is then ready to be packaged, for example in bags.

The present invention therefore provides a process for producing a high-performance powder (in particular cosmetic powder) of renewable origin, in which the initial product (prepolymer) undergoes few chemical conversions: principally primary mechanical conversions, such as milling or mechanical filtering. The process of the invention makes it possible to avoid the two steps of dissolution and precipitation, and does not require the use of solvents. It is therefore environmentally friendly. Furthermore, the method for producing a powder according to the invention leaves few residues, the latter being readily recyclable.

In addition, compared with the natural products (fruit stone powders, rice powder, bamboo powder, etc), the powders of the invention have the advantages of synthetic materials. Their characteristics (in particular their impurities) are completely controlled by the conditions of synthesis. The process of the invention limits the risks of contamination with toxic or allergenic compounds. The powders thus obtained are not contaminated from the bacteriological or mycological point of view and do not require a subsequent decontamination step or the addition of preservatives.

Examples 4 to 7 illustrate various embodiments of the process according to the invention, without however limiting it, and indicate the particle size characteristics of the powder obtained on a Cilas 920 particle sizer, operating by laser diffraction. The mill used in these examples is an opposed air jet mill (2 nozzles). It is a small pilot mill, with an air flow rate substantially equal to 100 m³/h (model: MultiNO 1290, manufacturer Schüttgutveredelung NOLL GmbH).

Example 4

A prepolymer in the form of chips of polyamide 11 (product A), having a relative viscosity of 0.45 (according to Arkema method: 0.5 g/dl in metacresol at 25° C.) is loaded into the double-cone, steel, batch bore mill. After a period of rotation of several hours, the powder is emptied out. The particle size obtained, measured on a Cilas 920 particle sizer, is:

| D50 = 15.6 μm | D10 = 7.6 μm | D90 = 26.2 μm |
| --- | --- | --- |

Example 5

Product A (cf. Example 4) is premilled in a mill/classifier to an average diameter of close to 90 μm, and then 1% of Aerosil 972 (supplier, Degussa AG) is added thereto, this percentage being given by mass relative to the total weight PA 11+silica. This powder is fed into an opposed air jet mill. The compressed air flow rate at 5 bar effective is 100 Nm³/h and the rotation speed of the classifier is 9000 rpm. The particle size of the powder obtained, measured on a Cilas 920 particle sizer, is:

| D50 = 10 μm | D10 = 1.6 μm | D90 = 19.6 μm |
| --- | --- | --- |

Example 6

A prepolymer in the form of chips of polyamide 11 (product B), having a relative viscosity of 0.3 (according to Arkema method: 0.5 g/dl in metacresol at 25° C.) and to which 1% by mass of Aerosil 972 has been added, is fed into an opposed air jet mill. The compressed air flow rate at 5 bar ($5 \times 10^5$ Pa) effective is 100 Nm³/h and the rotation speed of the classifier is 9000 rpm (revolutions per minute). The particle size of the powder obtained, measured on a Cilas 920 particle sizer, is:

| D50 = 5.1 μm | D10 = 1.2 μm | D90 = 11.5 μm |
| --- | --- | --- |

Example 7

A prepolymer in the form of chips of polyamide 11 (product B), having a relative viscosity of 0.3 (according to Arkema method: 0.5 g/dl in metacresol at 25° C.) and to which 1% by mass of Aerosil 972 has been added, is fed into an opposed air jet mill. The compressed air flow rate at 5 bar ($5 \times 10^5$ Pa) effective is 100 Nm³/h and the rotation speed of the classifier is 6000 rpm (revolutions per minute). The particle size of the powder obtained, measured on a Cilas 920 particle sizer, is:

| D50 = 8.9 μm | D10 = 1.5 μm | D90 = 18.4 μm |
| --- | --- | --- |

In fact, the process for the manufacture of ultrafine polyamide powder of the invention makes it possible to do away with the consumption of petroleum, to reduce energy consumption, and to make use of starter materials derived from the cultivation of plants. In addition, it has lower manufacturing costs and a favourable energy balance.

The invention claimed is:

1. A polyamide (PA) powder comprising a homopolyamide or copolyamide derived at least partially from renewable materials, in which particles of the powder have a nonspherical, irregular shape, without sharp edges, and a volume median diameter within the range of from 5 to 20 μm, an absorption capacity, measured according to the DIN ISO 787N standard, within the range of from 55 to 110 g of oil/100 g of polyamide powder and a breaking strength of said powder, when it is compacted only by compression under one tonne, within the range of from 100 to 600 Newtons.

2. The polyamide powder according to claim 1, comprising at least one molecule of: 11-aminoundecanoic acid, n-heptyl-11-aminoundecanoic acid, sebacic acid, decanediamine, a difatty acid, a dimer of a fatty acid or mixtures thereof.

3. The polyamide powder according to claim 1, wherein the PA is PA 11, PA 10.10 or a copolyamide comprising at least one of the following monomers: 11, 10.10, 10.36, 6.10, 10.T or mixtures thereof.

4. The polyamide powder according to claim 1, wherein said polyamide is entirely derived from renewable materials.

5. The polyamide powder according to claim 1, in which the particles have a specific surface area within the range of from 1 to 20 m²/g.

6. The polyamide powder according to claim 1, in which the particles have a volume median diameter within the range of from 5 to 15 μm.

7. The polyamide powder according to claim 1, wherein its absorption capacity, measured according to the DIN ISO 787N standard, within the range of from 60 to 90 g of oil/100 g of polyamide powder and a breaking strength of said powder, when it is compacted only by compression under one tonne, within the range of from 150 to 500 Newtons.

8. The polyamide powder according to claim 1, wherein a breaking strength of said powder, when it is compacted only by compression under one tonne, within the range of from 150 to 500 Newtons.

9. The polyamide powder according to claim 1, wherein it comprises $^{14}$C.

10. The polyamide powder according to claim 1, comprising at least 20% by mass of carbon of renewable origin.

11. The polyamide powder according to claim 1, comprising at least $0.2 \times 10^{-10}$% by mass of $^{14}$C.

12. A product comprising the polyamide powder of claim 1, wherein said product is a cosmetic, pharmaceutical or perfumery product, coating, paint, anticorrosive composition, additive for paper, object formed by melt agglomeration or radiation sintering, electrophoresis gel, multilayer composite material, packaging, toy, textile, automobile part or electronics industry part.

13. The product according to claim 12, wherein said polyamide powder is a compacting agent in pressed cosmetic formulations.

14. The product according to claim 12 wherein said polyamide powder is a matifying agent.

15. A process for preparing a polyamide powder according to claim 1, comprising:
   milling at ambient temperature a prepolymer powder having an inherent viscosity of less than 0.5 (0.5 g/dl in metacresol at 25° C.), said milling being carried out by means of an opposed air jet mill.

16. The process according to claim 15, in which the prepolymer has an inherent viscosity within the range of from 0.25 to 0.5.

17. The process according to claim 15, further comprising adding fumed silica to the prepolymer powder before it is milled.

18. The process according to claim 15, further comprising, before the milling:
   manufacturing a prepolymer of PA having a number-average molecular mass of less than 5000 g/mol, and having a viscosity of less than 0.5 (0.5 g/dl in meta-cresol at 25° C.).

19. The process according to claim 15, further comprising, after the milling:
   raising the viscosity of the milled prepolymer powder, to the final viscosity desired for the powder.

20. The process according to claim 19, in which the viscosity rise is performed by solid-phase polycondensation in a dryer.

21. The process according to claim 15, conducted in a solvent.

22. The process according to claim 15, in which the final particle size of the PA powder is adjusted directly by adjusting the milling speed.

23. The process according to claim 22, in which the adjustment of the milling speed is carried out by means of a selector integrated into the mill.

24. The product of claim 12, wherein said product is a cosmetic powder containing an additive comprising pigments, fillers, antioxidants or powder binders.

25. The product according to claim 24, wherein said additive comprises silica powder.

26. The product according to claim 24, wherein said product constitutes a face powder or an eye shadow.

* * * * *